United States Patent
Mathis et al.

(10) Patent No.: US 7,364,588 B2
(45) Date of Patent: Apr. 29, 2008

(54) DEVICE, ASSEMBLY AND METHOD FOR MITRAL VALVE REPAIR

(75) Inventors: Mark L. Mathis, Fremont, CA (US); Gregory Nieminen, Bothell, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 555 days.

(21) Appl. No.: 10/912,735

(22) Filed: Aug. 4, 2004

(65) Prior Publication Data
US 2005/0065598 A1 Mar. 24, 2005

Related U.S. Application Data

(63) Continuation of application No. 10/095,507, filed on Mar. 11, 2002, now Pat. No. 6,797,001.

(51) Int. Cl.
*A61F 2/06* (2006.01)
(52) U.S. Cl. .................. 623/2.37; 623/2.36
(58) Field of Classification Search ....... 623/2.36–2.37
See application file for complete search history.

(56) References Cited

U.S. PATENT DOCUMENTS

| | | | |
|---|---|---|---|
| 3,995,623 A | 12/1976 | Black et al. | |
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,441,515 A | 8/1995 | Khosravi et al. | |
| 5,474,557 A | 12/1995 | Mai | |
| 5,514,161 A | 5/1996 | Limousin | |

(Continued)

FOREIGN PATENT DOCUMENTS

EP 0893133 1/1999

(Continued)

OTHER PUBLICATIONS

Papageorgiou, P., et al., "Coronary Sinus Pacing Prevents Induction of Atrial Fibrillation," Circulation 96: 1893-1898, Sep. 16, 1977.

(Continued)

*Primary Examiner*—Suzette Gherbi
(74) *Attorney, Agent, or Firm*—Shay Glenn LLP

(57) ABSTRACT

A mitral valve therapy device effects the condition of a mitral valve annulus of a heart. The device includes an elongated member dimensioned to be placed in the coronary sinus of the heart adjacent the mitral valve annulus. The elongated member is flexible when placed in the heart in a first orientation to position the device in the coronary sinus adjacent the mitral valve annulus and relatively inflexible when rotated into a second orientation after the device is positioned in the coronary sinus adjacent to the mitral valve annulus to substantially straighten and increase the radius of curvature of the mitral valve annulus.

19 Claims, 2 Drawing Sheets

U.S. PATENT DOCUMENTS

| | | |
|---|---|---|
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,676,671 A | 10/1997 | Inoue |
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliott |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,015,402 A | 1/2000 | Sahota |
| 6,027,517 A | 2/2000 | Crocker et al. |
| 6,077,295 A | 6/2000 | Limon et al. |
| 6,077,297 A | 6/2000 | Robinson et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,210,432 B1 | 4/2001 | Solem et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,764,510 B2 | 7/2004 | Vidlund et al. |
| 6,776,784 B2 | 8/2004 | Ginn |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,821,297 B2 | 11/2004 | Snyders |
| 6,960,229 B2 | 11/2005 | Mathis et al. |
| 6,964,683 B2 | 11/2005 | Kowalsky et al. |
| 6,966,926 B2 | 11/2005 | Mathis |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |
| 2002/0161377 A1 | 10/2002 | Rabkin et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0083613 A1 | 5/2003 | Schaer |
| 2003/0088305 A1 | 5/2003 | Van Schie et al. |
| 2003/0105520 A1 | 6/2003 | Alferness et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0171776 A1 | 9/2003 | Adams et al. |
| 2003/0171806 A1 | 9/2003 | Mathis et al. |
| 2003/0212453 A1 | 11/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0111095 A1 | 6/2004 | Gordon et al. |
| 2004/0133240 A1 | 7/2004 | Adams et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220657 A1 | 11/2004 | Nieminen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0096666 A1 | 5/2005 | Gordon et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |

| | | | |
|---|---|---|---|
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0191121 A1 | 8/2006 | Gordon |
| 2007/0066879 A1 | 3/2007 | Mathis et al. |

FOREIGN PATENT DOCUMENTS

| | | |
|---|---|---|
| EP | 0893133 A1 | 1/1999 |
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| WO | WO 98/56435 A1 | 12/1998 |
| WO | WO 00/44313 A1 | 8/2000 |
| WO | WO 00/60995 A2 | 10/2000 |
| WO | WO 00/74603 A1 | 12/2000 |
| WO | WO 00/60995 A3 | 1/2001 |
| WO | WO 01/00111 A1 | 1/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/049647 A1 | 6/2003 |
| WO | WO 03/059198 A2 | 7/2003 |
| WO | WO 03/063735 A2 | 8/2003 |

OTHER PUBLICATIONS

Mathis et al., U.S. Patent Application entitled: "Device and Method for Modifying the Shape of a Body Organ", U.S. Appl. No. 10/429,172 filed May 2, 2003.

Heartsite.com. Echocardiogram. 1999; p. 1-4. A.S.M. Systems Inc. Available at: http://www.heartsite.com/html/echocardiogram.html. Accessed Jul. 1, 2005.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Gregory Nieminen. U.S. Appl. No. 11/458,040, entitled "Mitral Valve Annuloplasty Device with Twisted Anchor," filed Jul. 17, 2006 (WSGR Reference No. 29912-733.501).

Gregory Nieminen. U.S. Appl. No. 11/458,042, entitled "Mitral Valve Annuloplasty Device with Wide Anchor," filed Jul. 17, 2006 (WSGR Reference No. 29912-733.502).

Lucas Gordon, et al. U.S. Appl. No. 11/383,115 entitled "Tissue Shaping Device with Integral Connector and Crimp," filed May 12, 2006 (WSGR Reference No. 29912-730.401).

Mark L. Mathis, et al. U.S. Appl. No. 11/279,352, entitled "Mitral Valve Annuloplasty Device with Vena Cava Anchor," filed Apr. 11, 2006 (WSGR Reference No. 29912-739.201).

Clifton Alferness, et al. U.S. Appl. No. 11/467,105 entitled "Device and method for modifying the shape of a body organ," filed Aug. 24, 2006 (WSGR Reference No. 29912-705.304).

Mathis, Mark; U.S. Appl. No. 11/655,710, entitled "Mitral Valve Device Using Conditioned Shape Memory Alloy," filed Jan. 18, 2007 (SLG # 10057-714.301).

DEVICE, ASSEMBLY AND METHOD FOR MITRAL VALVE REPAIR

CROSS-REFERENCE

This application is a continuation application of Ser. No. 10/095,507, filed Mar. 11, 2002 now U.S. Pat. No. 6,797,001, which is incorporated herein by reference in its entirety and to which application we claim priority under 35 USC § 120.

FIELD OF THE INVENTION

The present invention generally relates to a device, assembly and method for treating dilated cardiomyopathy of a heart. The present invention more particularly relates to mitral valve annulus device, assembly, and method wherein the device is flexible when in a first orientation to conform to the coronary sinus adjacent the mitral valve annulus and relatively rigid when rotated into a second orientation to reshape the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Another approach to treat mitral regurgitation with a device in the coronary sinus is based upon the observation that the application of a localized force against a discrete portion of the mitral valve annulus can terminate mitral regurgitation. This suggests that mitral regurgitation may be localized and nonuniform. Hence, the device applies a force to one or more discrete portions of the atrial wall of the coronary sinus to provide localized mitral valve annulus reshaping instead of generalized reshaping of the mitral valve annulus. Such localized therapy would have all the benefits of the generalized therapy. In addition, a localized therapy device may be easier to implant and adjust.

A still further approach to treat mitral regurgitation from the coronary sinus of the heart contemplates a device having a first anchor configured to be positioned within and fixed to the coronary sinus of the heart adjacent the mitral valve annulus within the heart, a cable fixed to the first anchor and extending proximally from the first anchor within the heart, a second anchor configured to be positioned in and fixed in the heart proximal to the first anchor and arranged to slidingly receive the cable, and a lock that locks the cable on the second anchor. When the first and second anchors are fixed within the heart, the cable may be drawn proximally and locked on the second anchor. The geometry of the mitral valve is thereby effected. This approach provides flexibility in that the second anchor may be positioned and fixed in the coronary sinus or alternatively, the second anchor may be positioned and fixed in the right atrium. This approach further allows adjustments in the cable tension after implant.

A still further alternative for treating mitral regurgitation contemplates a device having a first anchor configured to be positioned within and anchored to the coronary sinus of the heart adjacent the mitral valve annulus within the heart. A second anchor is configured to be positioned within the heart proximal to the first anchor and adjacent the mitral valve annulus within the heart. A connecting member, having a fixed length, is permanently attached to the first and second anchors. As a result, when the first and second anchors are within the heart with the first anchor anchored in the coronary sinus, the second anchor may be displaced proximally to effect the geometry of the mitral valve annulus and released to maintain the effect on the mitral valve geometry. The second anchor may be configured, when deployed, to anchor against distal movement but be moveable proximally to permit the second anchor to be displaced proximally within the coronary sinus.

A further approach uses staple devices for effecting mitral valve annulus geometry of a heart. The staples are carried in an elongated catheter placeable in the coronary sinus of the heart adjacent the mitral valve annulus. The staples include first and second leg portions, each leg portion terminating in a tissue piercing end, and a connection portion extending between the first and second leg portions. The connection portions have an initial stressed and distorted configuration to separate the first and second leg portions by a first distance when the tissue piercing ends pierce the mitral valve annulus and a final unstressed and undistorted configuration after the tissue piercing ends pierce the mitral valve annulus to separate the first and second leg portions by a second distance, the second distance being shorter than the first distance. A tool forces the staples from the catheter to cause the tissue piercing ends of the first and second leg portions to pierce the mitral valve annulus with the connection portion of the at least one staple in the initial configuration. The catheter includes a tubular wall having breakaway slots adjacent the staples to permit the staples to be forced from the catheter into the adjacent tissue.

The present invention provides a still further approach for effecting mitral valve annulus geometry of a heart.

SUMMARY OF THE INVENTION

The invention provides a device that effects the condition of a mitral valve annulus of a heart. The device includes an elongated member dimensioned to be placed in the coronary sinus of the heart adjacent the mitral valve annulus, the elongated member having a relatively low resistance to flexure in a first direction and a relatively high resistance to flexure n a second direction. The first and second directions may lie in the same plane.

The elongated member may include a first longitudinal side facing the first direction and a first plurality of notches formed in the first longitudinal side to provide the elongated member with the relatively low resistance to flexure in the first direction. The elongated member may also include a second longitudinal side facing the second direction and a second plurality of notches formed in the second longitudinal side to render the elongated member stable when flexed in the second direction. The first plurality of notches are preferably larger than the second plurality of notches.

The elongated member also has first and second ends and an anchor at each end that fix the device in the coronary sinus. Preferably each anchor anchors the device against longitudinal movement and rotational movement.

The invention further provides a device that effects the condition of a mitral valve annulus of a heart including an elongated member dimensioned to be placed in the coronary sinus of the heart adjacent the mitral valve annulus. The elongated member is flexible when placed in the heart in a first orientation to position the device in the coronary sinus adjacent the mitral valve annulus and relatively inflexible when rotated into a second orientation after the device is positioned in the coronary sinus adjacent to the mitral valve annulus.

The elongated member has a first radius of curvature when in the first orientation and a second radius of curvature when in the second orientation. The first radius of curvature is less than the second radius of curvature.

The invention still further provides a method of effecting the condition of a mitral valve annulus of a heart. The method includes the steps of providing a mitral valve annulus therapy device including an elongated member that is flexible when placed in the heart in a first orientation and relatively inflexible when rotated into a second orientation, advancing the device into the coronary sinus of the heart with the device in the first orientation until the device is adjacent the mitral valve annulus within the coronary sinus, and rotating the device into the second orientation.

The method may further include the step of anchoring the device in the coronary sinus. The device is preferably anchored against at least rotational movement.

The invention still further provides an assembly that effects the condition of a mitral valve annulus of a heart. The assembly includes an elongated member dimensioned to be placed in the coronary sinus of the heart adjacent to the mitral valve annulus. The elongated member is flexible when placed in the heart in a first orientation to conform to the coronary sinus and relatively inflexible when rotated into a second orientation. The assembly further includes a push member configured to be releasably coupled to the elongated member that advances the elongated member into the coronary sinus adjacent to the mitral valve annulus.

The push member rotates the elongated member into the second orientation upon rotation of the push member. A U-joint releasably couples the elongated member to the push member.

The assembly may further include a flexible catheter having a lumen that receives the elongated member and push member to guide the elongated member into the coronary sinus. The elongated member may be rotated into the second orientation upon rotation of the catheter. The push member may be released from the elongated member with proximal movement of the catheter.

The elongated member has a first radius of curvature when in the first orientation and a second radius of curvature when in the second orientation. The first radius of curvature is less than the second radius of curvature. The elongated member also may have an anchor at each end that fix the device in the coronary sinus. The anchors preferably anchor the device against both longitudinal and rotational movement.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
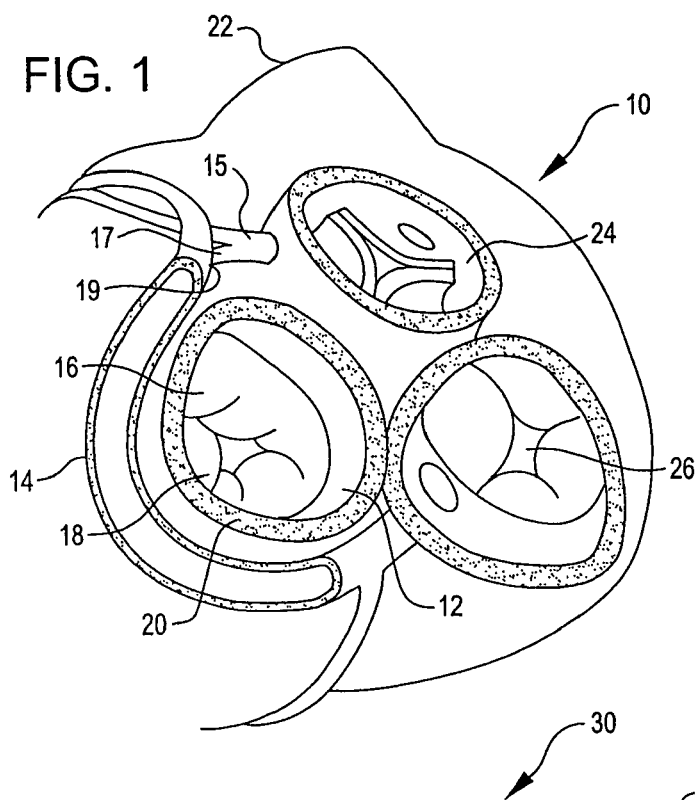
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
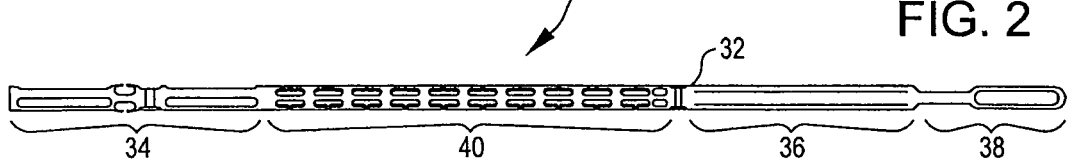
FIG. 2 is a side plan view of a mitral valve therapy device embodying the present invention.

FIG. 2 shows a mitral valve therapy device 30 embodying the present invention. The device 30 takes the form of an elongated tubular member 32 which includes a distal anchor 34, a proximal anchor 36, a coupler 38, and a therapy section 40.

The anchors 34 and 36 are shown in FIG. 2 in their predeployed configuration. As will be seen hereinafter, upon deployment of the device 30 in the coronary sinus, the anchors expand outwardly in a toggle bolt manner to anchor the device in the coronary sinus against both longitudinal and rotational movement. To that end, at least the anchors 34 and 36 are formed from a material, such as Nitinol, having shape memory to implement their expansion. The rest of the device 30 may also be formed from Nitinol or other non-rigid biocompatible materials such as stainless steel.

The coupler 38 releasably couples the device to a deployment tool to be described hereinafter during the implant and deployment of the device 30. The coupler forms with the deployment tool a U-joint to permit flexibility. As will also be seen hereinafter, the deployment tool includes a complementary coupler with shape memory for releasing the deployment tool from the elongated member 32.

Figure 3:
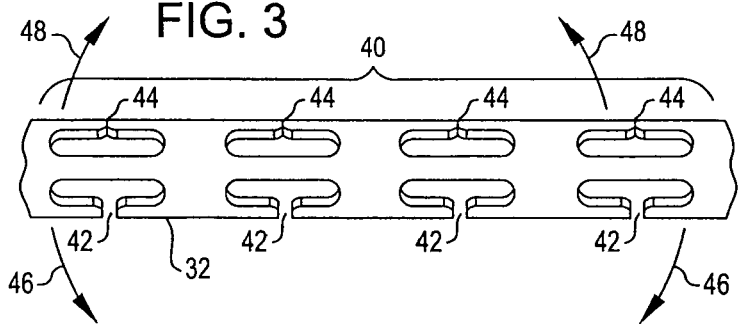
FIG. 3 is a side plan view to an enlarged scale of a portion of the device of FIG. 2.

FIG. 3 shows a portion of the therapy section 40 in greater detail. The elongated member 32, within the therapy section 40, is configured to permit a first flexibility in the elongated member when bent in a first direction and a second and less flexibility in the elongated member 32 when bent in a second direction. More specifically, the elongated member 32 includes a first plurality of slots or notches 42 along a side thereof and a second plurality of slots or notches 44 along an opposite side thereof. The first plurality of notches 42 render the elongated member flexible for bending in the first direction as indicated by arrows 46 and the second plurality of notches 44 render the elongated member flexible for bending in the second direction as indicate by arrows 48. The first plurality of notches 42 are wider or larger than the second plurality of notches 44 so that the elongated member 32 has a relatively low resistance to flexure or bending in the first direction 46 and a relatively high resistance to flexure or bending in the second direction 48.

The relative resistances to flexure allow the device 30 to be readily positioned in the coronary sinus of the heart and then deployed. While in a first orientation, with the first plurality of notches adjacent the mitral valve annulus, the device 30, as it is advanced into the coronary sinus, is permitted to bend and conform to the shape of the coronary sinus. Once properly positioned in the coronary sinus adjacent the mitral valve annulus, the device may be rotated into a second orientation wherein the second plurality of notches 44 are adjacent to the mitral valve annulus. The device 30 may be rotated by either rotating the deployment tool or by rotating a deployment catheter, to be described hereinafter, in which the device resides and which may be used to guide the device 30 into the proper position within the coronary sinus. Once rotated into the second orientation, the elongated member 32 will substantially straighten to act upon and increase the radius of curvature of the adjacent mitral valve annulus.

The second plurality of slots 44 permit slight bending of the elongated member towards the mitral valve annulus to render the device stable in the second orientation. Were the device not permitted to bend slightly towards the mitral valve annulus while in the second orientation, the device could revert to the then more stable first orientation away from the mitral valve annulus. This and further aspects of the present invention will be seen more fully with reference to FIGS. 4-6 which illustrate the deployment of the device 30 in accordance with an embodiment of the present invention.

Figure 4:
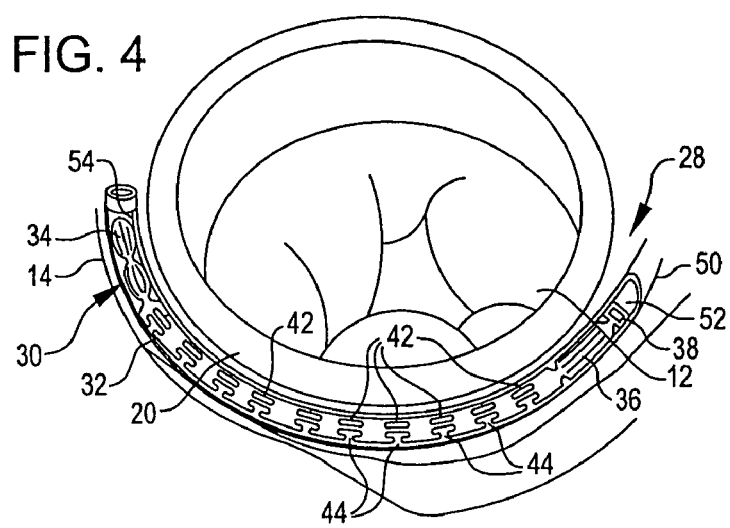
FIG. 4 is a partial superior view of a human heart illustrating a first step in the deployment of the mitral valve therapy device embodying the present invention.

FIG. 4 illustrates an assembly 28, including the device 30, for effecting the geometry of the mitral valve annulus 20. The assembly is illustrated in an initial stage of deploying the device 30. The assembly includes the device 30, a deployment catheter 50, and the deployment tool or push member 52. The distal end of the push member 52 is coupled to the coupler 38 of the device 30. Both the device 30 and push member 52 are within a lumen 54 of the deployment catheter 50 which is dimensioned to permit the device 30 and push member 52 to be advanced down into the coronary sinus in which the catheter 50 is already positioned.

As the device 30 is advanced into the coronary sinus and adjacent the mitral valve annulus, the device is disposed in the first orientation with the first plurality of notches 42 adjacent the mitral valve annulus 20. This permits the device 30 to bend with relatively low resistance to flexure to conform to the shape of the coronary sinus with a first radius of curvature. As a result, the device 30 may be readily positioned adjacent the mitral valve annulus 20.

Figure 5:
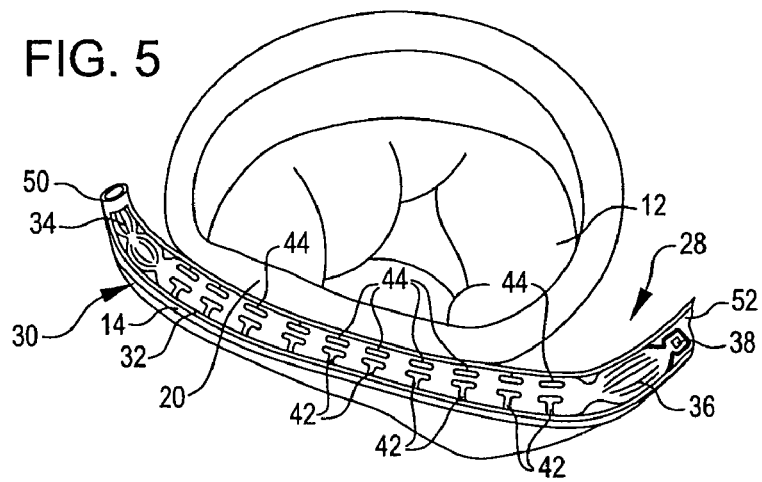
FIG. 5 is a view similar to FIG. 4 illustrating a further step in the deployment of the mitral valve therapy device.

With the device 30 positioned in the coronary sinus 14 adjacent the mitral valve annulus 20 as illustrated in FIG. 4, the device may now be rotated into the second orientation as illustrated in FIG. 5. In the second orientation, the second plurality of notches or slots 44 are now adjacent the mitral valve annulus. Because the second plurality of notches are relatively narrow, the higher resistance of flexure of the device in the second orientation will cause the device the substantially straighten to a second and increased radius of curvature. This causes the device to act upon the geometry of the mitral valve annulus 20 by increasing its radius of curvature as illustrated in FIG. 5 to treat and terminate mitral regurgitation, for example.

The device 30 may be rotated by rotating the deployment catheter 50 or by rotating the deployment tool 52 relative to the catheter 50. This permits the assembly 28 to remain intact while the effectiveness of the device placement is evaluated. Should moving the device to a slightly different position be required, this may be accomplished by simply rotating the device back to the first orientation and repositioning the device with the deployment tool 52.

With the device 30 positioned as shown in FIG. 5 and its effectiveness confirmed, the device 30 may now be fully deployed. To that end, the deployment catheter 50 is pulled proximally while the deployment tool or push member 52 is held stationary. This removes the catheter from the device 30.

Figure 6:
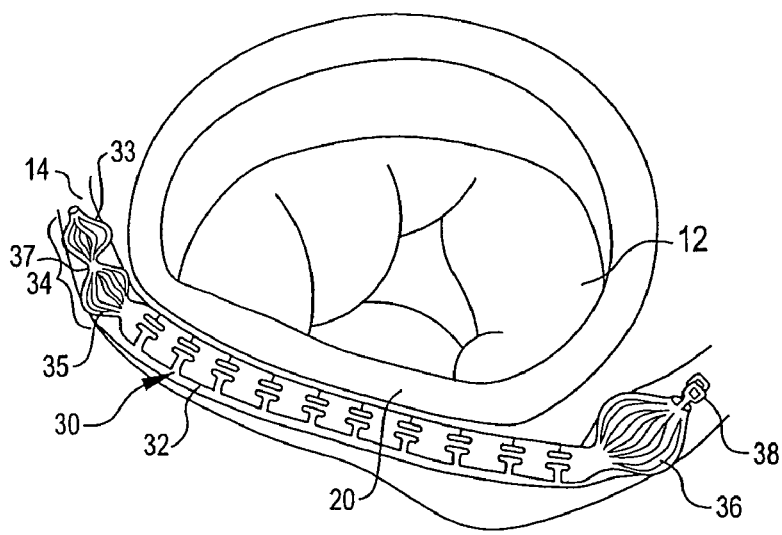
FIG. 6 is a superior view of a human heart similar to FIG. 4 illustrating the mitral valve therapy device deployed and anchored in the heart.

As illustrated in FIG. 6, the distal anchor 34 is released to expand in a toggle bolt like manner and anchor the device against both longitudinal and rotational movement. The distal anchor 34 is divided into a pair of sections 33 and 35 which are coupled together by a flexible coupling 37. This enables the anchor 34 to better conform to the bend in the coronary sinus at this location of the heart.

Further proximal movement of the deployment catheter 50 releases the proximal anchor 36. It also expands in a toggle bolt like manner to anchor the device against both longitudinal and rotational movement.

When the deployment catheter is moved proximally enough to expose the coupling 38, the coupling 38 is removed from the deployment tool. The deployment tool and the catheter may now be removed from the patient together. Hence, FIG. 6 illustrates the device 30 fully deployed and anchored without the deployment catheter or deployment tool.

Figure 7:
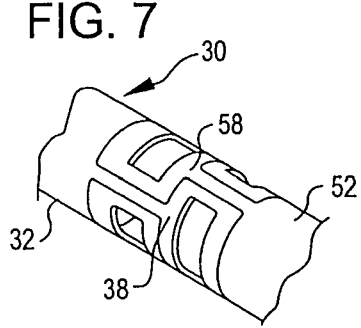
FIG. 7 is a partial perspective view of a coupling arrangement between the mitral valve therapy device and a deployment tool in accordance with an embodiment of the present invention.

FIGS. 6 and 7 show the coupling and decoupling of the device 30 and the deployment tool or push member 52 in greater detail. In FIG. 7 the coupler 38 is shown engaged with a complimentary coupler 58 of the deployment tool 52. The configuration of the couplers 38 and 58 form a U-joint allowing flexibility between the device 30 and the tool 52.

Figure 8:
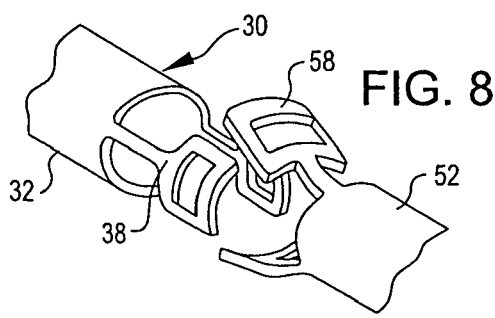
FIG. 8 is a partial perspective view illustrating the release of the coupling arrangement of FIG. 7.

The coupler 58 of the deployment tool 52 has shape memory for disengaging the coupler 38 of the device 30 when the catheter is moved sufficiently proximally to expose the couplers 38 and 58. This is illustrated in FIG. 8. Here it can be seen that the coupler 58 has sufficiently disengaged the coupler 38 of the device 30 to enable the deployment tool 52 to be removed from the patient with the fully deployed and anchored device 30 within the heart to provide its therapeutic effect as illustrated in FIG. 6.

While particular embodiments of the present invention have been shown and described, modifications may be made. It is therefore intended in the appended claims to cover all such changes and modifications which fall within the true spirit and scope of the invention.

What is claimed is:

1. A device that effects the condition of a mitral valve annulus of a heart comprising an elongated member dimensioned to be placed in the coronary sinus of the heart adjacent the mitral valve annulus, the elongated member having a relatively low resistance to flexure in a first direction and a relatively high resistance to flexure in a second direction, wherein the first and second directions lie in the same plane, the elongated member has first and second ends and the device includes an anchor at each end that fix the device in the coronary sinus.

2. The device of claim 1 wherein each anchor anchors the device against longitudinal movement and rotational movement.

3. The device of claim 1 wherein the first end anchor comprises an expandable anchor.

4. The device of claim 1 wherein the first end anchor comprises a first anchor section and a second anchor section coupled by a flexible coupling.

5. The device of claim 1 wherein the second end anchor comprises an expandable anchor.

6. An assembly that effects the condition of a mitral valve annulus of a heart comprising:

an elongated member dimensioned to be placed in the coronary sinus of the heart adjacent to the mitral valve annulus, the elongated member being flexible when placed in the heart in a first orientation to conform to the coronary sinus and relatively inflexible when rotated into a second orientation; and a deployment tool releasably coupled to the elongated member by a releasable coupling assembly.

7. The device of claim 6 wherein the coupling assembly comprises a first coupler associated with the deployment tool and a second coupler associated with the elongated member and complementary with the first coupler.

8. The device of claim 7 wherein the first coupler is adapted to change shape to release from the second coupler.

9. The device of claim 8 wherein the first coupler is formed from shape memory material.

10. The device of claim 7 wherein the first and second couplers form a U-joint.

11. The device of claim 6 wherein the coupling assembly is adapted to be flexible.

12. A method of effecting the condition of a mitral valve annulus of a heart, the method comprising:

providing a mitral valve annulus therapy device having a relatively low resistance to flexure in a first orientation and a relatively high resistance to flexure in a second orientation;

advancing the device with a deployment tool into the coronary sinus of the heart with the device in the first orientation, the deployment tool being connected to the device through a coupling assembly;

rotating the device into the second orientation; and releasing the device from the deployment tool by actuating the coupling assembly.

13. The method of claim 12 wherein the advancing step comprises permitting the device and deployment tool to flex about the coupling assembly.

14. The method of claim 12 further comprising anchoring a distal end of the device after the rotating step.

15. The method of claim 14 wherein the device comprises a distal anchor, the anchoring step comprising expanding the distal anchor.

16. The method of claim 12 further comprising anchoring a proximal end of the device after the rotating step.

17. The method of claim 14 wherein the device comprises a proximal anchor, the anchoring step comprising expanding the proximal anchor.

18. A method of effecting the condition of a mitral valve annulus of a heart, the method comprising:

providing a mitral valve annulus therapy device having a relatively low resistance to flexure in a first orientation and a relatively high resistance to flexure in a second orientation;

advancing the device with a deployment tool into the coronary sinus of the heart with the device in the first orientation, the deployment tool being connected to the device through a coupling assembly;

rotating the device into the second orientation; and releasing the device from the deployment tool by actuating the coupling assembly, wherein the coupling assembly comprises a first coupler associated with the deployment tool and a second coupler associated with the elongated member and complementary with the first coupler, the actuating step comprising separating the first coupler from the second coupler.

19. The method of claim 18 wherein the separating step comprises changing a shape of the first coupler.

* * * * *